United States Patent
Kobayashi

[11] Patent Number: 5,299,573
[45] Date of Patent: Apr. 5, 1994

[54] TONOMETER

[75] Inventor: Kazunobu Kobayashi, Yokohama, Japan

[73] Assignee: Canon Kabushiki Kaisha, Tokyo, Japan

[21] Appl. No.: 998,052

[22] Filed: Dec. 29, 1992

[30] Foreign Application Priority Data

Jan. 8, 1992 [JP] Japan ................. 4-020420

[51] Int. Cl.⁵ .............................................. A61B 3/16
[52] U.S. Cl. ..................................... 128/645; 128/652
[58] Field of Search ................................ 128/645–652

[56] References Cited

U.S. PATENT DOCUMENTS

| | | | |
|---|---|---|---|
| 4,817,620 | 4/1989 | Katsuragi et al. | 128/648 |
| 4,825,873 | 5/1989 | Kohayakawa | 128/648 |
| 4,951,670 | 8/1990 | Tanaka et al. | 128/648 |
| 4,991,584 | 2/1991 | Kobayashi et al. | |
| 5,076,274 | 12/1991 | Matsumoto | 128/648 |

FOREIGN PATENT DOCUMENTS 54-38437 3/1979 Japan.
61-321 1/1986 Japan.

Primary Examiner—Lee S. Cohen
Assistant Examiner—J. Lacyk
Attorney, Agent, or Firm—Fitzpatrick, Cella Harper & Scinto

[57] ABSTRACT

A non-contact type tonometer in which an air is sprayed on an eye to be examined to deform the cornea and measure the intraocular pressure of the eye to be examined. The tonometer is provided with a cylinder, a piston for compressing the air in the cylinder, a deformation detection system for detecting deformation of the cornea sprayed with the air, and a driving system for driving the piston and having a piston driving spring and a spring operation mechanism. When a measurement is performed, the force is accumulated in the spring, then released by the mechanism.

7 Claims, 3 Drawing Sheets

TONOMETER

BACKGROUND OF THE INVENTION

1. Field of the Invention

The present invention relates to a tonometer and, more particularly, to a non-contact tonometer for spraying a compressive fluid on an eye to be examined to deform the cornea and measuring the intraocular pressure of the eye to be examined in accordance with a deformed state of the cornea.

2. Related Background Art

A conventional non-contact tonometer of this type generally uses air as the compressive fluid. For example, as disclosed in Japanese Laid-Open Patent Application Nos. 54-38437 and 61-321, air in a compression chamber is gradually compressed by a piston driven by a solenoid, and the compressed air is sprayed on the cornea of the eye to be examined through a nozzle to measure a period of time required to cause the cornea to assume a predetermined aplanation condition, thereby obtaining the intraocular pressure of the eye to be examined.

However, the solenoid or a solenoid driving power supply for driving the piston to deform the cornea within a very short period of time requires a relatively large force. Therefore, a conventional tonometer tends to be large and bulky.

Recent demand has arisen for a more compact, simpler tonometer.

SUMMARY OF THE INVENTION

It is the first object of the present invention to provide a tonometer having a more compact, simpler arrangement.

The above and other objects, features, and advantages of the present invention will be apparent from the detailed description of the preferred embodiments given below in conjunction with the accompanying drawings.

DESCRIPTION OF THE PREFERRED EMBODIMENTS

According to each embodiment to be described later, a non-contact tonometer is disclosed in which a compressive fluid in a compression chamber is compressed by a piston, the compressed fluid is sprayed on the cornea of an eye to be examined in accordance with the difference between the internal and external pressures of the compression chamber, and an intraocular pressure is calculated by an intraocular pressure detecting means in accordance with the deformation of the cornea. The piston is driven by releasing a spring in which a force is accumulated.

In the non-contact tonometer having the arrangement described above, the compressed spring is released to drive the piston, thereby compressing the compressive fluid. The compressed fluid is sprayed on the cornea of the eye to be examined to deform the cornea. The intraocular detecting means detects the deformation of the cornea and calculates the intraocular pressure of the eye to be examined.

Each embodiment will be described in detail with reference to the accompanying drawings.

Figure 1:
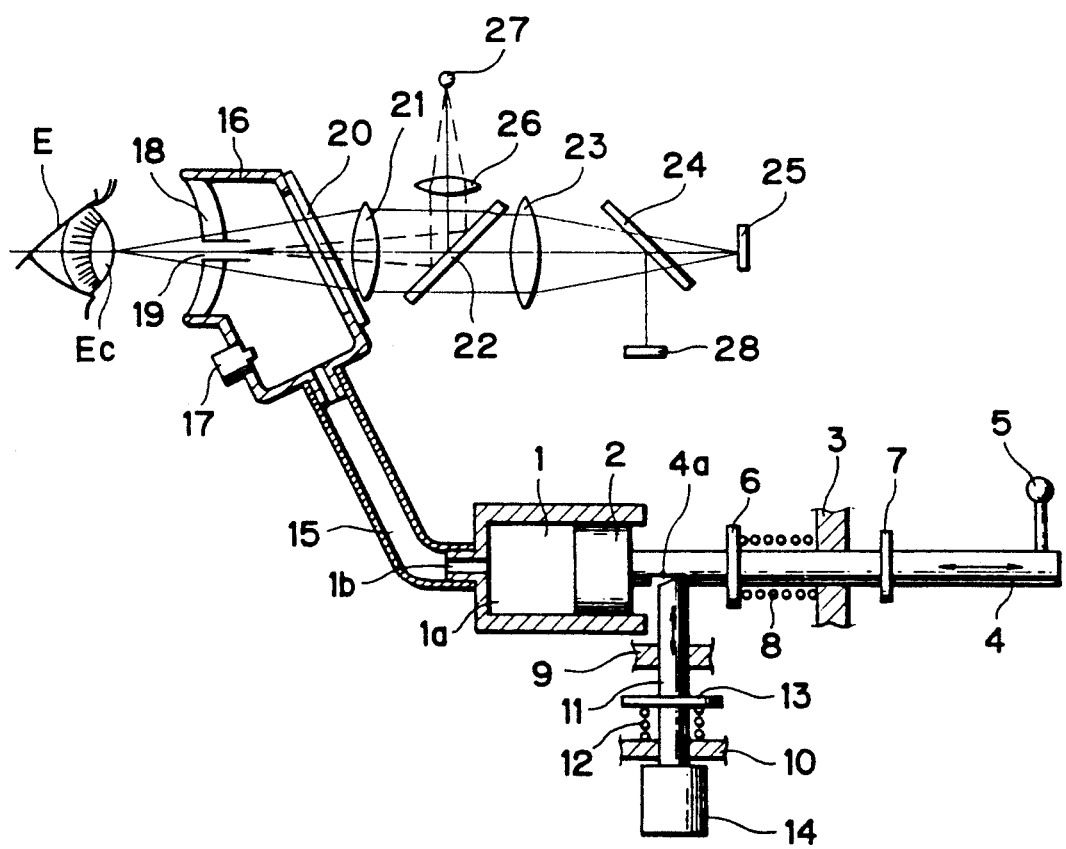
FIG. 1 is a view showing an arrangement of the first embodiment of the present invention.

A non-contact tonometer of the first embodiment shown in FIG. 1 comprises a compressed air generating unit for generating compressed air and a detection unit for detecting a deformation amount of an eye E to be examined. The compressed air generating unit comprises a cylinder 1, a piston 2 for compressing air in a chamber 1a of the cylinder 1, and a rod-like piston shaft 4 moved together with the piston 2 in a direction in which the air is compressed in the chamber 1a. A lever 5 extends from an end portion of the piston shaft 4. Collar-like snap rings 6 and 7 are fitted on the piston shaft 4 to interpose a fixed wall 3 therebetween. A coil spring 8 is wound around the piston shaft 4 between the snap ring 6 and the fixed wall 3. The coil spring 8 biases the piston 2 inward in the chamber 1a, and the snap ring 7 limits any excessive movement of the piston 2. A notch 4a is formed downwardly in the piston shaft 4 near the piston 2. An upper end portion of a rod-like stopper shaft 11 extending upwardly and supported by two fixed walls 9 and 10 is locked in the notch 4a in a state wherein the volume of the chamber 1a is increased and the coil spring 8 is compressed. A coil spring 12 and a snap ring 13 are fitted on the stopper shaft 11, and a solenoid 14 is arranged at the lower end of the stopper shaft 11 to instantaneously drive the stopper shaft 11 downward so as to cause the stopper shaft 11 to always bias the piston shaft 4. A nozzle port 1b is formed on the surface of the cylinder 1 at a position opposite to the piston 2 and is connected to a chamber 16 of the detection unit through a pipe 15.

In the detection unit, the hollow chamber 16 is defined to face the eye E. A pressure sensor 17 is arranged on the inner surface of the chamber 16 to measure the internal pressure. A concave half mirror 18 is incorporated in the front surface of the chamber 16 which opposes the eye E, so that the person to be examined can perform alignment by himself or herself. A spray nozzle 19 is formed at the center of the half mirror 18. A transparent plate 20 provided behind the chamber 16, an objective lens 21, a beam splitting member 22, a condenser lens 23, a beam splitting member 24, and a measurement photoelectric sensor 25 are arranged behind the nozzle 19 in the other named. A lens 26 and a light source 27 are arranged in the reflection direction of the beam splitting member 22. An alignment photoelectric sensor 28 is arranged in the reflection direction of the beam splitting member 24.

Before measurement, an operator pulls the lever 5 until the stopper shaft 11 is locked in the notch 4a, so that the volume in the chamber 1a of the cylinder 1 is large. Since the notch 4a serves as a stopper for locking the stopper shaft 11, the piston shaft 4 will not return to the original position even if the operator releases the lever 5.

The light source 27 always emits light. The light beam emitted from the light source 27 passes through the lens 26, is reflected by the beam splitting member 22, and reaches the eye E through the objective lens 21, the transparent plate 20, and the concave half mirror 18. A light beam reflected by the eye E passes through the concave half mirror 18, the transparent plate 20, the objective lens 21, the beam splitting member 22, and the condenser lens 23, and a part of the transmitted light beam is reflected by the beam splitting member 24 and detected by the alignment photoelectric sensor 28. The remaining part of the transmitted light passes through the beam splitting member 24 and is detected by the measurement photoelectric sensor 25.

Figure 2:
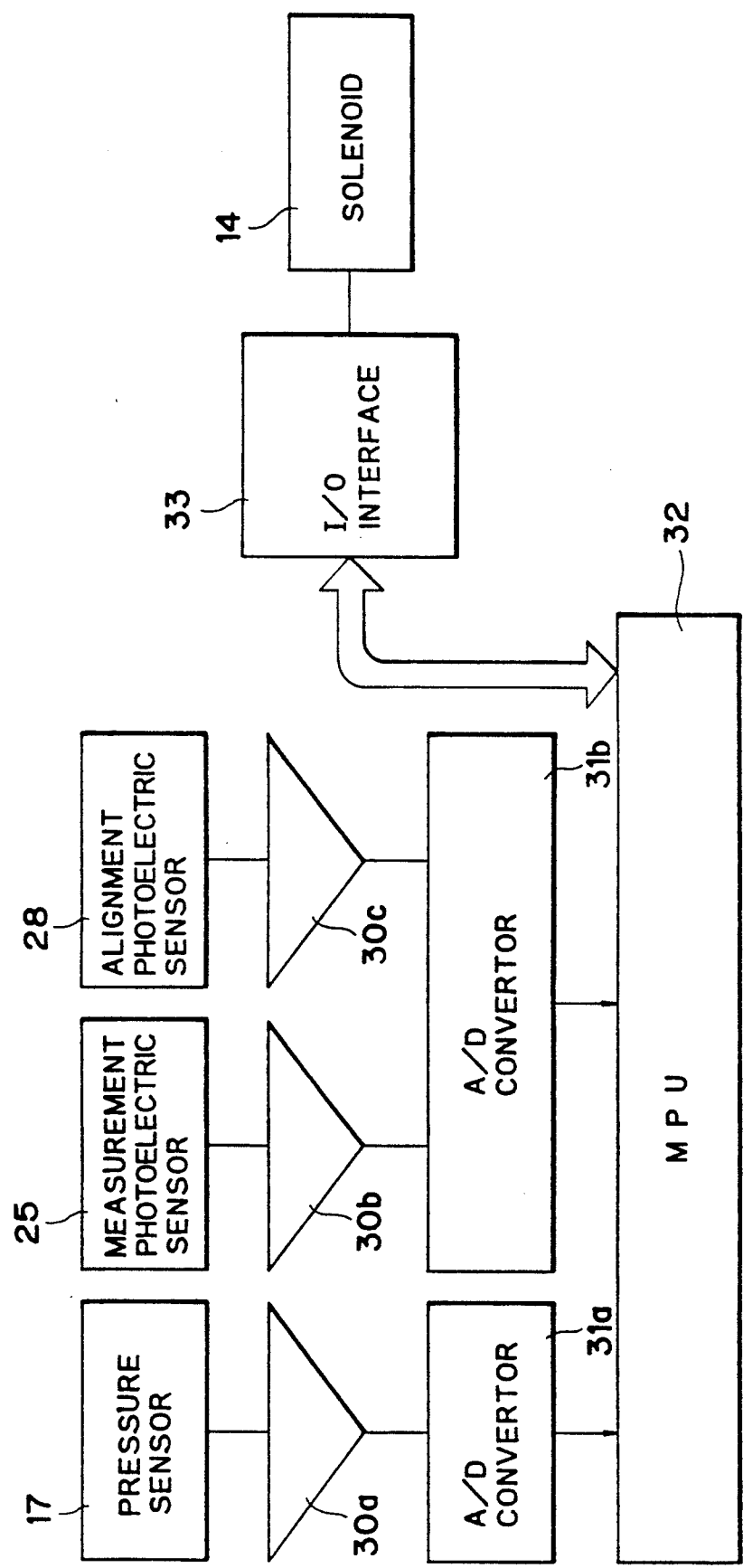
FIG. 2 is a block diagram of a detection/ control system of the first embodiment.

FIG. 2 is a block diagram of the detection/control system of the first embodiment. Signals from the pressure sensor 17, the measurement photoelectric sensor 25, and the alignment photoelectric sensor 28 are sent to an MPU 32 so as to perform various arithmetic operations and control through signal amplifiers 30a, 30b, and 30c and A/D converters 31a and 31b. The solenoid 14 is connected to the MPU 32 through an I/O interface 33, and control is performed in accordance with the signals from the pressure sensor 17, the measurement photoelectric sensor 25, and the alignment photoelectric sensor 28.

The person to be examined adjusts the position of his or her eye E while confirming it through the concave half mirror 18. When a coincidence between the position of the eye E and a predetermined position is confirmed in accordance with the signal from the alignment photoelectric sensor 28, the solenoid 14 is driven to move the stopper shaft 11 downward At this time, since the stopper shaft 11 is disengaged from the notch 4a, the piston 2 is moved together with the piston rod 4 by the force of the coil spring 8 in a direction in which the air in the cylinder 1 is compressed. The compressed air is introduced into the chamber 16 through the pipe 15 and is sprayed on a cornea Ec of the eye E through the spray nozzle 19. The degree of deformation of the cornea Ec is obtained from the signal from the measurement photoelectric sensor 25, and the pressure of the compressed air sprayed from the spray nozzle 19 is obtained from the signal from the pressure sensor 17. The degree of deformation and the pressure of the compressed air are synthetically analyzed in accordance with a known technique, thereby calculating the intraocular pressure of the eye E.

Figure 3:
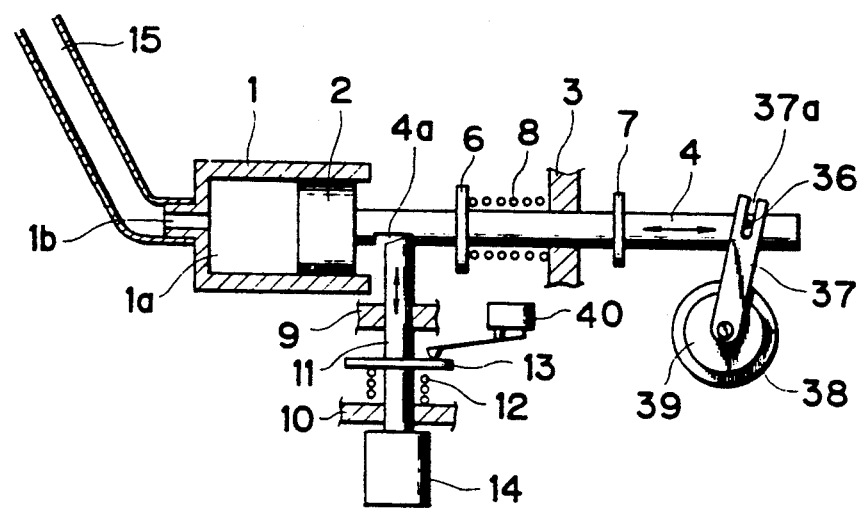
FIG. 3 is a view showing an arrangement of the second embodiment of the present invention.

FIG. 3 is a view showing an arrangement of the second embodiment. The same reference numerals as in the first embodiment denote the same members in the second embodiment. In the second embodiment, the coil spring 8 manually compressed in the first embodiment is automatically compressed. A pin 36 in place of the lever 5 extends on a piston shaft 4. An arm 37 having an elongated arm groove 37a having one open end is engaged with the pin 36 and is connected to a clutch 39 through a motor 38. The arm 37 is adapted to pivot together with the clutch 39. A microswitch 40 abuts against a snap ring 13 of a stopper shaft 11 to detect the engaged/nonengaged state of the stopper shaft 11. A releasing switch (not shown) is separately arranged to normally open the clutch 39.

Figure 4:
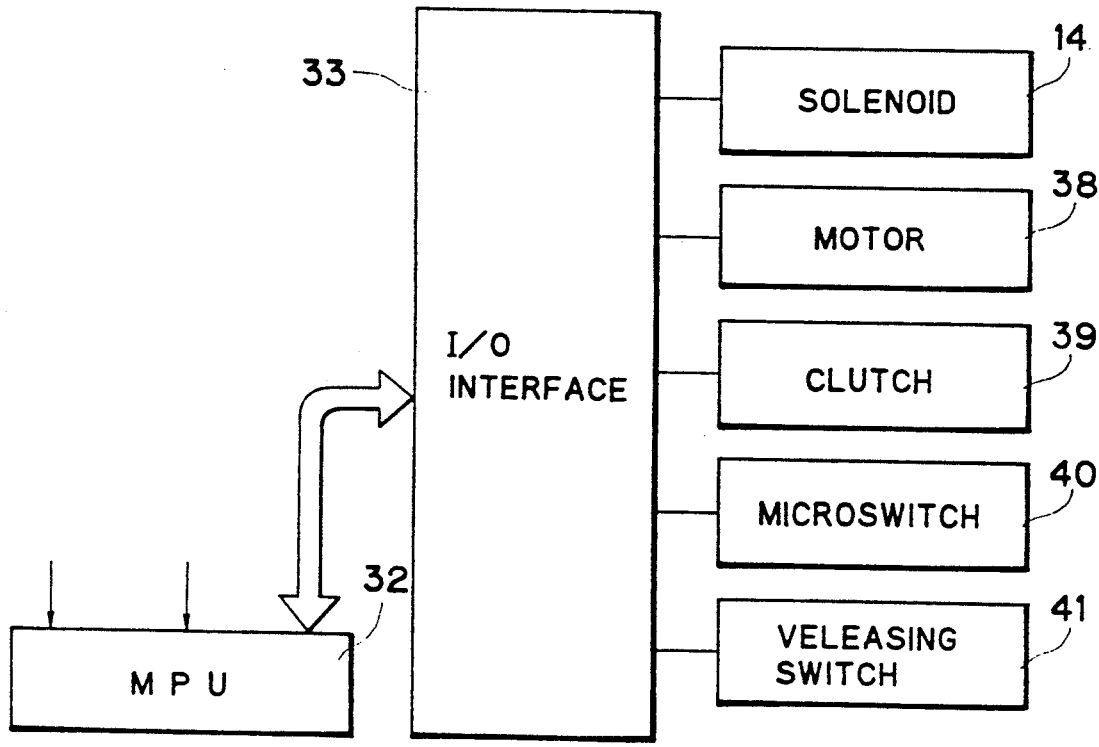
FIG. 4 is a block diagram of a detection/ control system of the second embodiment.

FIG. 4 is a block diagram of the detection/control system of the second embodiment. A solenoid 14, the motor 38, the clutch 39, the microswitch 40, and a releasing switch 41 are connected to an MPU 32 through an I/O interface 33 and are synthetically controlled.

In a measurement preparing condition, the motor 38 is gradually rotated while the clutch 39 is kept coupled to the motor 38. The arm 37 pulls the pin 36 to gradually compress the coil spring 8. When the piston 2 is pulled to a predetermined position and the stopper shaft 11 is locked in a notch 4a, movement of the stopper shaft 11 is detected by the microswitch 40. Thus, the motor 38 is stopped, and at the same time the clutch 39 is released. In this state, compression of the coil spring 8 is completed, and intraocular tension measurement is performed in the same manner as in the first embodiment.

When the intraocular pressure measurement is completed, the motor 38 and the clutch 39 are coupled to each other for the next measurement, so that the coil spring 8 is compressed again. Upon completion of all measurements, the releasing switch 41 is operated to release the clutch 39, so that weakening of compression of the coil spring 8 can be prevented. If the releasing switch 41 incorporates a timepiece function and the clutch 39 is automatically released upon a lapse of a predetermined period of time from the last measurement, the tonometer can be made to be more convenient.

As has been described above, a non-contact tonometer according to the present invention uses a spring for driving a piston and charges up the spring manually or by means of a motor to instantaneously generate mechanical energy as in the conventional measurement, thereby providing a more compact, lightweight tonometer. In addition, the tonometer can be portable and of a self-measurement type.

What is claimed is:

1. A tonometer comprising:
   a cylinder having a spray port at a position opposing an eye to be examined;
   a piston means for compressing a fluid in said cylinder, the fluid compressed by said piston means being sprayed on a cornea of the eye from the spray port;
   a deformation detection system means for detecting deformation of the cornea sprayed with the fluid from the spray port, an intraocular pressure of the eye being measured by using a detection result of said deformation detection system means; and
   a driving system means for driving said piston means and including a piston driving spring and a spring operation mechanism means for accumulating a force in said piston driving spring and releasing said piston driving spring which has accumulated the force upon driving of said piston means.

2. A tonometer according to claim 1, further comprising an internal pressure sensor means for measuring an internal pressure of said cylinder, the intraocular pressure of the eye being measured on the basis of the detection result of said deformation detection system means and a detection result of said internal pressure sensor means.

3. A tonometer according to claim 1, further comprising an alignment detection system means for detecting an aligned state of the eye with respect to said tonometer.

4. A tonometer according to claim 3, wherein said spring operation mechanism means releases said piston driving spring which has accumulated the force on the basis of a detection result of said alignment detection system means.

5. A tonometer according to claim 1, wherein said spring operation mechanism means causes said piston driving spring to automatically accumulate the force in a measurement preparation stage and releases the piston driving spring which has accumulated the force upon the performing of a measurement operation.

6. A tonometer according to claim 1, wherein said piston means has a piston rod, and said piston driving spring comprises a coil spring wound around said piston rod.

7. A tonometer according to claim 1, wherein said piston means has a piston rod having a notch, and said spring operation mechanism means has a stopper engaged with the notch, so that the force is accumulated in said piston driving spring while said stopper is kept engaged with the notch, and said piston driving spring is released when said stopper is disengaged from the notch.

* * * * *

UNITED STATES PATENT AND TRADEMARK OFFICE
CERTIFICATE OF CORRECTION

PATENT NO. : 5,299,573
DATED : April 5, 1994
INVENTOR(S) : KAZUNOBU KOBAYASHI

It is certified that error appears in the above-indentified patent and that said Letters Patent is hereby corrected as shown below:

TITLE PAGE
[57] ABSTRACT
    Line 1, "an" should be deleted.

SHEET 3 OF THE DRAWINGS
    In Fig. 4
    "VELEASING" should read --RELEASING--.

COLUMN 3
    Line 24, "downward" should read --downward.--.

Signed and Sealed this

Thirteenth Day of September, 1994

Attest:

BRUCE LEHMAN

Attesting Officer    Commissioner of Patents and Trademarks